United States Patent [19]
Vigil et al.

[11] Patent Number: 5,746,716
[45] Date of Patent: May 5, 1998

[54] CATHETER FOR INJECTING FLUID MEDICATION INTO AN ARTERIAL WALL

[75] Inventors: Dennis M. Vigil, San Diego; Peter Barath, Los Angeles, both of Calif.

[73] Assignee: InterVentional Technologies Inc., San Diego, Calif.

[21] Appl. No.: 500,121

[22] Filed: Jul. 10, 1995

[51] Int. Cl.$^6$ .................................. A61M 29/00
[52] U.S. Cl. .................. 604/97; 604/104; 606/194
[58] Field of Search .............. 606/1, 159, 190–204, 606/96–104

[56] References Cited

U.S. PATENT DOCUMENTS

| | | |
|---|---|---|
| 2,816,552 | 12/1957 | Hoffman . |
| 3,635,223 | 1/1972 | Klieman . |
| 4,318,400 | 3/1982 | Peery et al. . |
| 4,465,072 | 8/1984 | Taheri . |
| 5,009,659 | 4/1991 | Hamlin et al. . |
| 5,112,305 | 5/1992 | Barath et al. . |
| 5,242,397 | 9/1993 | Barath et al. . |
| 5,279,565 | 1/1994 | Klein et al. . |
| 5,282,785 | 2/1994 | Shapland et al. . |
| 5,286,254 | 2/1994 | Shapland et al. . |
| 5,295,962 | 3/1994 | Crocker et al. . |
| 5,306,250 | 4/1994 | March et al. . |
| 5,322,508 | 6/1994 | Viera . |
| 5,336,178 | 8/1994 | Kaplan et al. . |
| 5,354,279 | 10/1994 | Hofling . |
| 5,364,356 | 11/1994 | Hofling . |
| 5,370,614 | 12/1994 | Amundson et al. . |
| 5,571,086 | 11/1996 | Kaplan et al. . |
| 5,599,306 | 2/1997 | Klein et al. . |
| 5,609,574 | 3/1997 | Kaplan et al. . |

FOREIGN PATENT DOCUMENTS

| | | |
|---|---|---|
| 0 399 712 | 11/1990 | European Pat. Off. . |
| 0 567 788 A1 | 3/1993 | European Pat. Off. . |
| WO94/23787 | 10/1994 | WIPO . |

*Primary Examiner*—Glenn K. Dawson
*Attorney, Agent, or Firm*—Nydegger & Associates

[57] ABSTRACT

A device for injecting medication into a vessel wall includes an inflatable balloon mounted on a catheter. Additionally, a tubular sleeve surrounds the balloon to create an infusion chamber between the sleeve and the balloon, and a plurality of injectors are mounted on the sleeve in fluid communication with the infusion chamber. During use of the device, the balloon is first positioned in a vessel and then inflated to embed the injectors into the vessel wall. Next, a fluid medicament is introduced into the infusion chamber for further infusion from the chamber and through the injectors into the vessel wall.

18 Claims, 2 Drawing Sheets

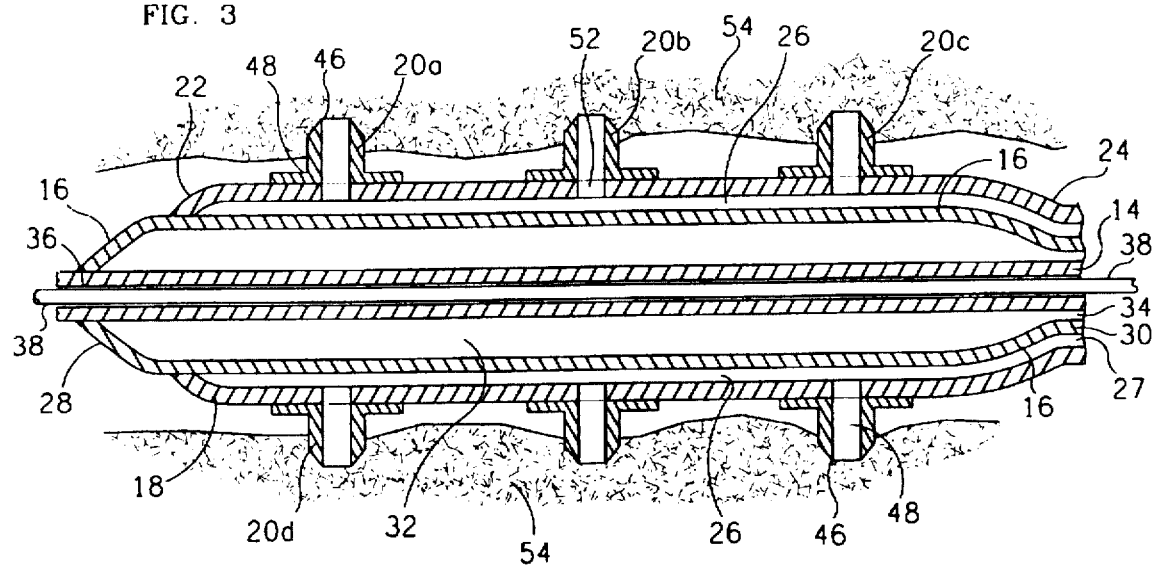
FIG. 3
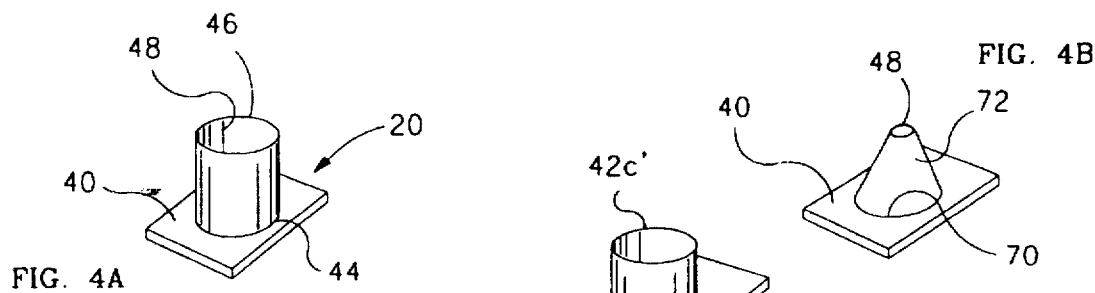
FIG. 4A
FIG. 4B
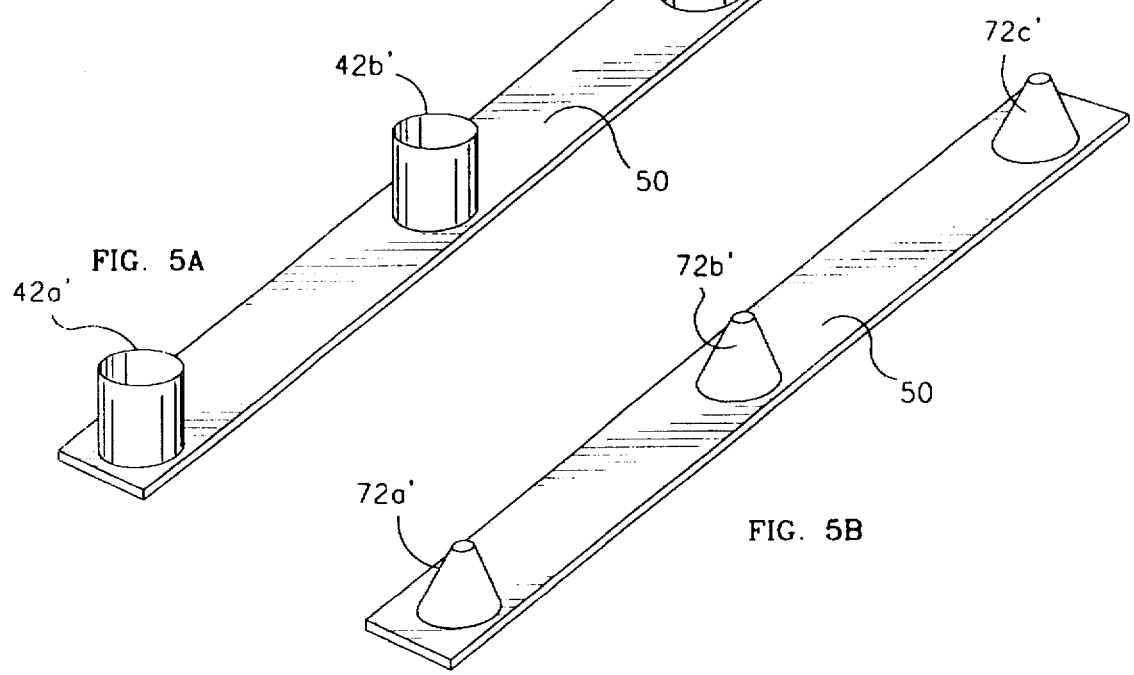
FIG. 5A
FIG. 5B

CATHETER FOR INJECTING FLUID MEDICATION INTO AN ARTERIAL WALL

FIELD OF THE INVENTION

The present invention pertains generally to invasive medical devices which are useful for the purpose of infusing fluid medicaments into a patient. More specifically, the present invention pertains to medical devices which can be inserted into a vessel of a patient's cardiovascular system. The present invention is particularly, but not exclusively, useful for infusing fluid medicaments directly into a vessel wall.

BACKGROUND OF THE INVENTION

Depending on the particular ailment it is known in the medical field that fluid medications can be infused directly into the wall of a vessel of a patient's cardiovascular system with beneficial results. For example, one such application involves the administration of medicaments into an arterial wall which will inhibit or prevent the restenosis of plaque in the artery. Any procedure involving the direct infusion of fluid medicaments into a vessel wall, however, requires the consideration of several factors. First, the procedure must be safe. For instance, due to the toxic nature of some medicaments, such a procedure must insure that only minimal amounts of medication are ever washed away into the blood stream and not actually infused into the vessel wall. Second, the device which infuses the medication into the vessel wall must be easy to use, accurate in its delivery capability and reliable in its operation.

Several devices have been suggested for the purpose of infusing fluid medicaments directly into a vessel wall. One example of such a device is disclosed in U.S. Pat. No. 5,354,279 which issued to Hofling for an invention entitled "Plural Needle Injection Catheter". The specific device disclosed in this patent employs prebent hollow needles which are extendable from a catheter to penetrate into a vessel wall. The extended needles are then used for infusion of the fluid medicament. U.S. Pat. No. 5,354,279 also discloses that an inner hose, which is so elastic that it can be expanded balloon-like, can be utilized to move the needles outwardly so as to engage or even pierce the surrounding vessel walls. Also, U.S. Pat. No. 5,364,356, was issued to Hofling for another invention entitled "Sleeve Catheter". This second patent to Hofling discloses a device which employs a balloon expandable sleeve that delivers fluid medication to a vessel wall. More specifically, this device of Hofling's includes a reconfigurable sleeve which is expanded by an inflatable balloon. It is intended that, as the sleeve expands, openings which are formed into the sleeve spread to discharge fluid medications onto the surface of the vessel walls. Still another example of a device for medicating a vessel wall is disclosed in U.S. Pat. No. 5,112,305 which issued to Barath et al. for an invention entitled "Catheter Device for Intramural Delivery of Therapeutic Agents". This same device is also disclosed in a related U.S. Pat. No. 5,242,397 which issued to Barath et al. for an invention entitled "Catheter Device and Method of Use for Intramural Delivery of Protein Kinase C and Tyrosine Protein Kinase Inhibitors to Prevent Restenosis after Balloon Angioplasty". Specifically, the device disclosed by Barath et al. employs a balloon which requires an initial slow filling of the balloon with a medicament to expand the balloon and position the balloon's surface against the vessel wall. This initial slow filling is then followed by a rapid filling of the balloon which reconfigures tubular extensions on the surface of the balloon for the infusion of medicaments through the tubular extensions and into the vessel wall.

None of the above discussed devices, however, address the problem from the same perspective as the present invention. Specifically, the present invention recognizes that it is preferable to have a mechanism for infusing medication into a vessel wall which is independent and separately operable from the mechanisms which position the device in the artery and which cause at least one medication injector to penetrate into the vessel wall. Consequently, as recognized by the present invention, it is preferable to isolate the mechanism for actual infusion of medications into the vessel wall from other operable mechanisms of the device. Further, the present invention recognizes that, depending on the nature and condition of the vessel wall, it is preferable to have the capability of selectively applying a variable force to the injectors of the device as they penetrate into the vessel wall.

In light of the above, it is an object of the present invention to provide a device for injecting medication into the wall of a vessel which includes a mechanism for penetrating a vessel wall with medication delivery injectors that is separate from the mechanism which infuses the medication into the vessel wall. It is another object of the present invention to provide a device for injecting medication into the wall of a vessel which can selectively vary the force that is used to penetrate the vessel wall with a fluid medication injector. Still another object of the present invention is to provide a device for injecting medication into the wall of a vessel which is easy to use, relatively simple to manufacture and comparatively cost effective.

SUMMARY OF THE INVENTION

In accordance with the present invention, a device for injecting medication into the wall of a vessel includes an inflatable PET balloon which is mounted on a multi-lumen catheter. A flexible tubular sleeve, preferably made of polyurethane, is provided. This sleeve effectively surrounds most of the inflatable balloon, and thereby creates an infusion chamber between the balloon and the sleeve. To create this chamber, the distal end of the tubular sleeve is attached directly onto the surface of the balloon, and the proximal end of the sleeve is extended proximally from the balloon. The open proximal end of the tubular sleeve thus establishes a port for fluid access into the infusion chamber.

For the device of the present invention, a plurality of injectors are mounted directly onto the sleeve and are placed in fluid communication with the infusion chamber. More specifically, each injector includes a base plate and a hollow protrusion which projects from the base of the injector to create a fluid channel through the injector. To establish a fluid path from the infusion chamber through the channel of the injector, the base of the injector is mounted onto the tubular sleeve over holes that may either be preformed into the sleeve or formed into the sleeve after the injectors have been attached to the sleeve.

The device of the present invention also includes a system for selectively inflating the balloon. As intended for the present invention, the balloon inflating system can be directly connected to a lumen of the catheter. The catheter lumen, in turn, is in fluid communication with the interior of the inflatable balloon. Additionally, the device includes a fluid pump which is engageable in fluid communication with the infusion chamber between the balloon and the sleeve for injecting fluid medicaments from a fluid source into the infusion chamber. Further, in an alternate embodiment of the present invention, instead of having single port injectors, a plurality of hollow protrusions can be formed onto the same base plate to create an injector having a plurality of outlet ports.

In the operation of the device of the present invention, a guidewire is first positioned into an artery of the patient. This is done to establish a mechanical pathway through the artery to the site where the fluid medication is to be infused. The extracorporeal end of the guidewire is then inserted into a lumen of the catheter and the balloon on the catheter is advanced over the guidewire and to the site where the medication is to be infused.

Once the balloon has been properly positioned for the infusion of fluid medicaments into the arterial wall, the balloon is inflated. This inflation of the balloon, in turn, urges the tubular sleeve to move outwardly with the expansion of the balloon. This action also causes the injectors to penetrate into the arterial wall. After the balloon has been inflated, and while the injectors remain penetrated into the arterial wall, the fluid pump is activated to inject fluid from the fluid source into the infusion chamber. Importantly, this pumping action also forces fluid from the infusion chamber through the injectors and into the arterial wall.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which:

FIG. 3 is a cross-sectional view of the device of the present invention as seen along the line 3—3 in FIG. 2 and positioned in an artery of a patient for infusion of fluid medications into the arterial wall;

FIG. 4A is a perspective view of an embodiment for a single port injector of the present invention;

FIG. 4B is a perspective view of another embodiment for a single port injector of the present invention;

FIG. 5A is a perspective view of an embodiment of a multi-port injector of the present invention; and FIG. 5B is a perspective view of another embodiment of a multi-port injector of the present invention.

DESCRIPTION OF THE PREFERRED EMBODIMENTS

Figure 1:
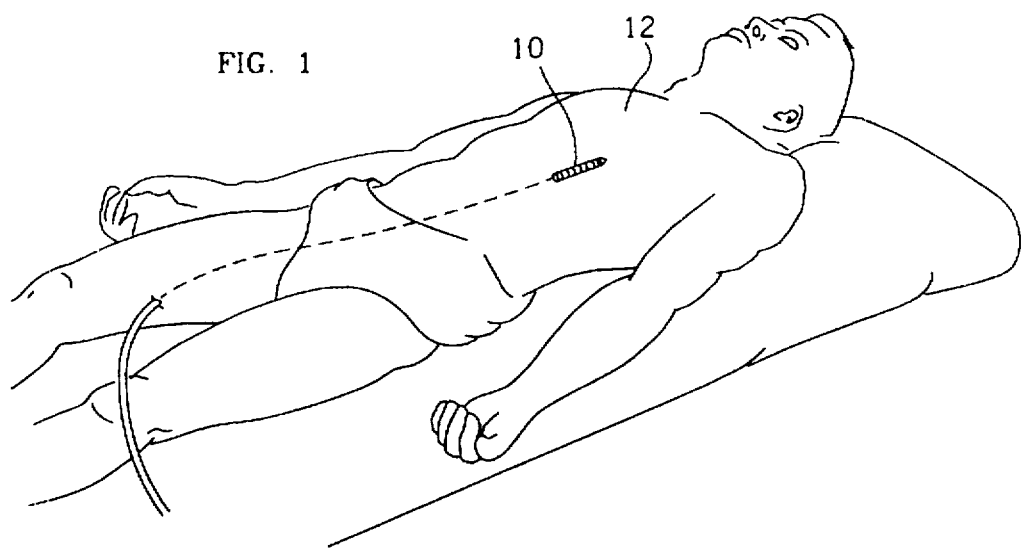
FIG. 1 is a perspective view of a patient with the catheter of the present invention positioned in an artery of the patient for operation of the device.

Referring initially to FIG. 1, a device for injecting fluid medication into the wall of a vessel in accordance with the present invention is shown and generally designated 10. More specifically, the device 10 is shown positioned in the artery of a patient 12. As will be appreciated by the skilled artisan, the device 10 is shown schematically positioned in the patient 12, and it is to be understood that use of the device 10 is not confined to only upper body arteries and vessels but, instead, can be used in arteries and vessels throughout the patient 12.

Figure 2:
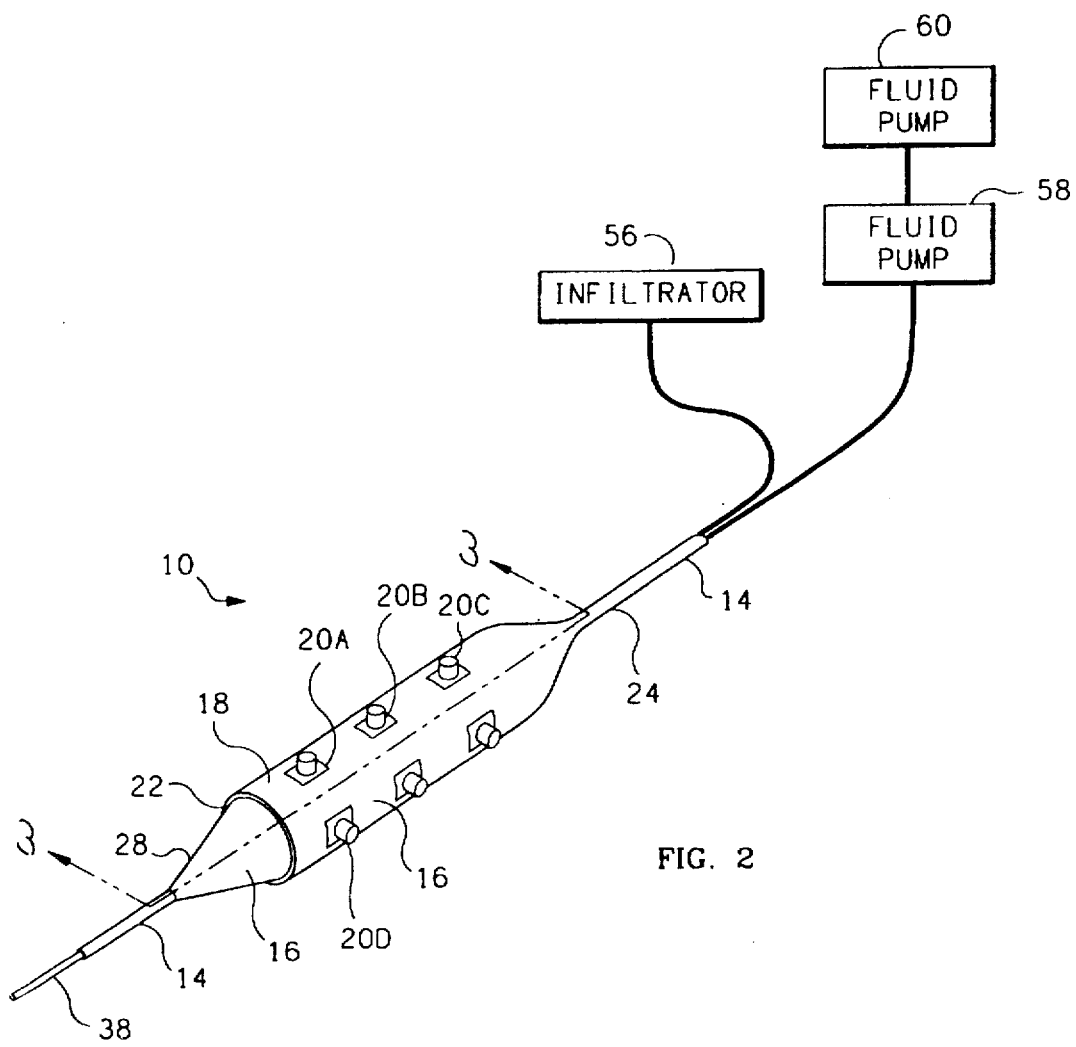
FIG. 2 is a perspective view of the device of the present invention.

FIG. 2 clearly shows that the components of device 10 include a multi-lumen catheter 14 which has an inflatable balloon 16 mounted thereon. Further, FIG. 2 indicates that a tubular sleeve 18 surrounds a substantial portion of the inflatable balloon 16, and that a plurality of injectors 20 are mounted onto the sleeve 18. Of these, the injectors 20a–20b are only exemplary. For purposes of the present invention, balloon 16 is preferably made of polyethylene terephthalate (PET). Additionally, the sleeve 18 can also be made of polyethylene terephthalate (PET).

A more complete appreciation of the structural cooperation between balloon 16, sleeve 18 and the injectors 20 is provided by FIG. 3 wherein it will be seen that the distal end 22 of sleeve 18 is attached directly to the surface of balloon 16. FIG. 3 also shows that the tubular sleeve 18 substantially surrounds the balloon 16 and that the proximal end 24 of sleeve 18 extends proximally from and beyond the balloon 16 over catheter 14. With this structural relationship, an infusion chamber 26 is formed between the balloon 16 and the sleeve 18. Additionally, as best seen in FIG. 3, a fluid port 27 is formed between the sleeve 18 and catheter 14 through which fluid medication can be injected into the infusion chamber 26.

FIG. 3 further shows that the distal end 28 of balloon 16 is affixed to the catheter 14, and that the proximal end of the balloon 16 closes onto the catheter 14 to create an inflation chamber 32 in the interior of the balloon 16. A port 34 is shown which provides fluid access into the inflation chamber 32. For purposes of the present invention, the port 34 can be connected in fluid communication with a lumen (not shown) of the catheter 14. FIG. 3 also shows that catheter 14 is formed with a lumen 36 which is dimensioned to receive a guidewire 38 therethrough.

Turning now to FIG. 4A, an injector 20 is shown to include a base plate 40 and a hollow protrusion 42 which projects therefrom. Further, it is seen that the end 44 of body 42 is affixed to or integral with the base plate 40. Preferably, the injector 20 is made of nickel and the protrusion 42 is formed by punching out the base plate 40. In any event, a cutting edge 46 is formed around the end of body 42 that is opposite from the end 44 on plate 40 and the resultant structure establishes a fluid channel 48 which extends through the injector 20. As shown, the injector 20 has a substantially cylindrical shaped protrusion 42.

In FIG. 4B, another embodiment for an injector of the present invention is shown and designated 70. Rather than having a cylindrical shaped protrusion 42 like the injector 20, however, the injector 70 has a substantially conical shaped protrusion 72. Like injector 20, the injector 70 is preferably made of nickel and is formed to have a fluid channel 48 which extends through the injector 70.

For a multi-port injector version of the present invention, a plurality of protrusions 42 can be formed from the same base plate. FIG. 5A shows such an embodiment. Specifically, FIG. 5A shows an elongated base plate 50 from which the protrusions 42a', 42b' and 42c' have been formed. In all important respects, the protrusions 42' shown in FIG. 5A are structurally the same as the protrusion 42 discussed above with reference to FIG. 4A. The only difference being that they are collectively mounted on the same base plate 50. Similarly, FIG. 5B shows a multi-port injector wherein the protrusion 72a', 72b' and 72c' have been formed from a base 50. In all important respects, the protrusions 72' shown in FIG. 5B are structurally the same as the protrusion 72 discussed above with reference to FIG. 4B. Again, the only difference being that they are collectively mounted on the same base plate 50.

For purposes of the present invention, the injectors 20 are mounted onto the sleeve 18 so that the channel 48 of each respective injector 20 is aligned with a hole 52 in the sleeve 18. This is done to establish fluid communication between the particular injector 20 and the infusion chamber 26. As a practical matter, it may be preferable in the construction of the device 10 to first mount the injector 20, 70 onto sleeve 18, which can be done in any manner well known in the pertinent art, such as by bonding, and then pierce the sleeve 18 through the channel 48.

In the operation of the present invention the guidewire 38 is first positioned in the vessel to establish a mechanical path for the device 10 to the site, as shown in FIG. 3, where fluid medications are to be infused into a vessel wall 54. Once the balloon 16 of device 10 is properly positioned, an inflator 56 is activated to inflate the balloon 16. As shown in FIG. 2, inflator 56 is connected to the proximal (extracorporeal) end of the device 10. Referring back to FIG. 3, it will be appreciated that, as balloon 16 is inflated, the expanding balloon 16 urges against the tubular sleeve 18 and causes the sleeve 18 to likewise expand. Consequently, the injectors 20,70 which are mounted on the surface of sleeve 18 move radially from the catheter 14 and are embedded into the vessel wall 54.

With the injectors 20,70 embedded into the vessel wall 54, the fluid pump 58 shown in FIG. 2 is activated to pump fluid from the fluid source 60 into the infusion chamber 26 through the port 34. Importantly, this pumping action also causes any fluid medication which has already been pumped into the infusion chamber 26 to be expelled through the channels 48 of injectors 20,70 and into the tissue of vessel wall 54.

After the fluid medication from fluid source 60 has been infused into the vessel wall 54, the balloon 16 can be deflated by reversing the inflator 56. This action will cause the balloon 16 to collapse and to thereby withdraw the injectors 20,70 from the vessel wall 54. The entire device 10 can then be withdrawn from the patient 12 over the guidewire 38.

While the particular device for injecting medication into the wall of a vessel as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

I claim:

1. A device for injecting a fluid into a wall of a vessel which comprises:

an inflatable balloon;

a tubular sleeve having a proximal end and a distal end having an external outer surface, said distal end of said tubular sleeve substantially encircling a portion of said balloon to create an infusion chamber therebetween;

at least one injector mounted on an outer surface of said tubular sleeve with said sleeve positioned between said injector and said balloon, said injector being in fluid communication with said infusion chamber;

means for inflating said balloon to embed said injector into the vessel wall; and means connected with said proximal end of said tubular sleeve for selectively injecting the fluid into said infusion chamber and through said injector into the vessel wall.

2. A device as recited in claim 1 wherein said injector comprises:

a base; and a hollow protrusion having a first end and a second end, said protrusion projecting from said base to establish a fluid channel through said base and through said protrusion, said first end of said protrusion being affixed to said base and said second end formed with a cutting edge.

3. A device as recited in claim 2 further comprising a plurality of said protrusions projecting from said base.

4. A device as recited in claim 3 which comprises a plurality of injectors.

5. A device as recited in claim 2 wherein said protrusion is substantially cylindrical shaped.

6. A device as recited in claim 2 wherein said protrusion is substantially conical shaped.

7. A device as recited in claim 1 which further comprises:

a guidewire;

a catheter formed with a plurality of lumens, one said lumen being dimensioned to receive said guidewire therethrough for guiding and positioning said balloon in said vessel.

8. A device as recited in claim 7 wherein one said lumen of said catheter establishes fluid communication between said balloon and said inflating means.

9. A device as recited in claim 1 wherein said inflatable balloon is made of polyethylene terephthalate (PET) and said tubular sleeve is made of polyurethane.

10. A method for injecting medication into a wall of a vessel using a device which includes an inflatable balloon, a tubular sleeve having a distal end with an external, outer surface which substantially encircles a portion of said balloon to create an infusion chamber therebetween, at least one injector mounted on the outer surface of said tubular sleeve with said sleeve positioned between said injector and said balloon, and said injector being in fluid communication with said infusion chamber, said method comprising the steps of:

positioning said balloon in the vessel;

inflating said balloon to embed said injector into the vessel wall and dilate said vessel with said balloon; and selectively injecting medication into said infusion chamber and through said injector into the vessel wall.

11. A device for injecting fluid from a fluid source into a wall of a vessel, the device comprising:

an inflatable balloon movable between a first configuration and an expanded second configuration;

at least one injector having a base;

interconnecting means which substantially encircle a portion of said inflatable balloon and move with the inflatable balloon between the first configuration for inserting the device into the vessel and the second configuration for embedding each injector into the wall of the vessel, the interconnecting means having an external outer surface for retaining the base of the injector to the interconnecting means, the interconnecting means defining at least a portion of an infusion chamber for connecting the fluid source with the injector in fluid communication; and means for selectively releasing fluid from the injector, independent of the inflatable balloon.

12. A device as recited in claim 11 wherein said injector further comprises;

a hollow protrusion having a first end and a second end, said protrusion projecting from said base to establish a fluid channel through said base and through said protrusion, said first end of said protrusion being affixed to said base and said second end formed with a cutting edge.

13. A device as recited in claim 11 which comprises a plurality of said injectors.

14. A device as recited in claim 11 wherein said interconnecting means includes a tubular sleeve having a proximal end and a distal end, said distal end of said tubular sleeve being surroundingly mounted over a portion of said inflatable balloon to create the infusion chamber therebetween.

15. A device as recited in claim 14 further comprising means connected with said proximal end of said tubular sleeve for injecting medication into said infusion chamber and through said injector into the vessel wall.

16. A method for delivering a fluid from a fluid source to a treatment area in a vessel wall, the method comprising the steps of:

advancing a balloon in the vessel while the balloon is at a first configuration, until the balloon is positioned substantially adjacent the treatment area, the balloon including a tubular sleeve which substantially encircles a portion of the balloon and at least one injector having a base which is secured to an external, outer surface of the tubular sleeve;

expanding the balloon to a larger, second configuration so that: a cutting edge of said at least one injector, which moves with the balloon and extends away from the balloon, penetrates the treatment area; and selectively releasing the fluid from the injector into the treatment area.

17. A device for injecting a fluid from a fluid source into a treatment area in a wall of a vessel, the device comprising:

an inflatable balloon that at least can be expanded from a first configuration to a larger, second configuration;

a plurality of injectors, each injector is suitable for penetrating the treatment area and releasing the fluid into the treatment area when the balloon is substantially in the second configuration, each injector comprises a substantially tubular protrusion defining a fluid channel for the fluid, the tubular protrusion having a base and an open, cutting edge which extends away from the balloon for penetrating the treatment area and releasing the fluid into the treatment area;

a tubular sleeve which substantially encircles at least a portion of the inflatable balloon and moves with the inflatable balloon, the tubular sleeve having an external outer surface for securing the base of the injectors to the tubular sleeve; and means for establishing fluid communication between the fluid source and at least one injector.

18. The device of claim 17 wherein the tubular sleeve cooperates with an outer surface of the balloon to define at least a portion of the means for establishing fluid communication.

* * * * *